United States Patent [19]

Nürnberg et al.

[11] Patent Number: 5,382,601
[45] Date of Patent: Jan. 17, 1995

[54] MEMANTINE-CONTAINING SOLID PHARMACEUTICAL DOSAGE FORMS HAVING AN EXTENDED TWO-STAGE RELEASE PROFILE AND PRODUCTION THEREOF

[75] Inventors: Eberhard Nürnberg, Uttenreuth/Welher; Erhard Seiller, Nidderau; Stefan Ritsert, Eberbach, all of Germany

[73] Assignee: Merz + Co. GmbH & Co., Frankfurt am Main, Germany

[21] Appl. No.: 96,952

[22] Filed: Jul. 23, 1993

[30] Foreign Application Priority Data

Aug. 4, 1992 [DE] Germany .............................. 4225730

[51] Int. Cl.⁶ .......................... A61K 9/38; A61K 9/64; A61K 37/16
[52] U.S. Cl. ................... 514/775; 530/360; 424/465; 424/469; 424/470
[58] Field of Search .................. 424/465, 469, 470; 514/775; 530/360

[56] References Cited

U.S. PATENT DOCUMENTS

| | | | |
|---|---|---|---|
| 3,594,467 | 7/1971 | Christenson et al. ................. | 424/19 |
| 4,076,846 | 2/1978 | Natsuka et al. ....................... | 426/62 |
| 4,122,193 | 10/1978 | Scherm et al. ....................... | 424/330 |
| 4,127,650 | 11/1978 | Buehler .................................. | 424/184 |
| 4,346,112 | 8/1982 | Henkel et al. ........................ | 424/325 |
| 4,665,081 | 5/1987 | Doi et al. . | |
| 4,816,177 | 3/1989 | Nelson et al. ........................ | 424/465 |
| 4,853,377 | 8/1989 | Pollack ................................... | 514/161 |
| 4,897,380 | 1/1990 | Pollack et al. ........................ | 514/23 |
| 5,061,703 | 10/1991 | Bormann et al. .................... | 514/212 |
| 5,068,109 | 11/1991 | Foldager et al. ..................... | 424/441 |
| 5,167,962 | 12/1992 | Lew et al. ............................. | 424/426 |

FOREIGN PATENT DOCUMENTS

0447100  9/1991  European Pat. Off. .
2207353A  2/1989  United Kingdom .

OTHER PUBLICATIONS

Pharm. Acta Helv. 66, No. 4, 120–124 (1991), "Effect of Low-molecular Casein and Gelatin on Absorption of Ibuprofen after Oral and Rectal Administration"; S. Kimura, et al.

Pharmaceutical Technology 9, 360–374 (1990), "Influence of Sodium Caseinate on the Dissolution Rate of Hydrochlorothiazide and Chlorothiazide", F. C. Millar, et al.

Primary Examiner—Shep K. Rose
Attorney, Agent, or Firm—Gordon W. Hueschen

[57] ABSTRACT

The present invention provides solid pharmaceutical compositions in dosage form containing an active ingredient or principle, preferably memantine, which exhibit an extended two-phase release profile and which are characterized by the presence of both a water-soluble and a water-insoluble salt of casein, preferably sodium and calcium caseinate, in the matrix thereof, in broad proportions and in a total amount between 5 and 98% by weight of the composition, and with a process for the production thereof.

22 Claims, 3 Drawing Sheets

MEMANTINE-CONTAINING SOLID PHARMACEUTICAL DOSAGE FORMS HAVING AN EXTENDED TWO-STAGE RELEASE PROFILE AND PRODUCTION THEREOF

BACKGROUND OF THE INVENTION

1. Field of Invention

The present invention is concerned with solid pharmaceutical compositions in dosage form which exhibit an extended matrix-controlled two-phase release profile and which are characterized by the presence in the matrix of both a water-soluble and a water-insoluble salt of casein, preferably sodium and calcium caseinate, respectively, in a total amount between 5 and 98% by weight of the composition, and with a process for the production thereof. A part or all of the insoluble casein salt may be replaced by a salt or solution of a polyvalent including bivalent cation, e.g., the calcium cation, adapted to form the water-insoluble casein salt in situ. The invention is particularly suitable for the provision of solid pharmaceutical dosage forms in which the active substance or principle is memantine.

2. Background of the Invention and Prior Art

Solid oral drug compositions or preparations having a retarded release, so-called retarder or extended-release preparations, are products from which the active ingredient is released over an extended period of time and hence exhibit a prolonged effect, with resultant plasma levels being adapted to therapeutic requirements. Also, a polyphase release profile can be employed to attain the desired therapeutic objectives. However, this does not necessarily mean that long-lasting effective blood level concentrations are consistently achieved. Moreover, systemic side effects and undesirable local effects within the gastrointestinal tract due to excessive local concentrations and resulting erratic plasma levels, respectively, are to be avoided.

In conventional procedures for the preparation of solid pharmaceutical dosage forms having an extended-release profile or pattern, the active substance in the majority of cases is either given extended-release properties by the application of various coatings or by being embedded in a macromolecular substance from which it is slowly released.

The most important control procedures for the release of an active pharmaceutical from a solid dosage form are the film-coating and the matrix procedures. In film coating procedures, film-forming polymers are employed to provide sustained release of the active substance in a diffusion-controlled manner. However, such an approach is disadvantageous if, during ingestion of the oral dosage form, the film is prematurely breached, as by chewing or abrasion, thereby releasing an excessive amount of active ingredient, which can result in undesirable effects from such excessive single-shot drug release.

In the matrix-controlled release approach, lipophilic substances, e.g., higher alcohols, waxes, or insoluble thermoplasts, are employed, it being a disadvantage that synthetic polymers not only generally contain varying amounts of undesirable monomers but that moreover a complete release of drug from the matrix is frequently not effected in practice.

The U.S. Pat. No. 4,665,081 describes a nifedepin formula for oral administration, which contains casein and inorganic additives selected from magnesium silicate, oxide, or aluminatemetasilicate, synthetic hydrotalc and magnesium aluminum oxide, thereby ensuring that the active substance—provided that a gastric juice-resistant auxiliary agent is included—is not released in the stomach but is rather rapidly released in the intestine. Such formulation will cause, on the one hand, a retarded release relative to the time of administration but, on the other hand, due to the rapid dissolution in the intestine, a high plasma concentration which is likely to result in undesirable side effects.

Pharm. Acta Helv. 66, No. 4, 120–124 (1991) describes an ibuprofen formula containing casein or gelatine which causes an elevated rate of dissolution and release, respectively, of the active substance.

Pharmaceutical Technology 9, 360–374 (1990) examines the influence of the presence of sodium caseinate on the rate of release of an active substance. Here, too, an enhanced dissolution, in particular, of chlorothiazide and hydrochlorothiazide, is reported.

The EP-A 0 447 100 Patent discloses formulations permitting controlled release in the stomach and in the intestine in response to the enzymes contained therein. For this purpose, a gel matrix, e.g., of alginate or carboxymethyl cellulose, carragheenin, or the like is employed, which contains imbedded therein a protein, such as calcium caseinate, and which comprises a further drug or food substance which is bondable to the protein. Although a controlled release is enabled thereby, such effect is achieved by the incorporation of protein in a surrounding matrix-forming gel.

GB-A 2 207 353 also describes formulations with a controlled release, containing calcium-free mixtures of alginic acid salts and caseinate. The protracted release is, however, based on a surrounding gel-matrix principle of the type referred to above.

It is apparent to one skilled in the art that the available technology for effective and reliable extended release, especially multistage release pharmaceutical dosage forms, still leaves much to be desired.

OBJECTS OF THE INVENTION

It is accordingly an object of the present invention to provide a pharmaceutical dosage form which is characterized by an extended controlled-release profile such that the active substance can be conveniently and reliably released over an extended period in at least two (2) stages and a process for the production thereof. Other objects of the invention will become apparent hereinafter, and still others will be obvious to one skilled in the art to which the present invention pertains.

SUMMARY OF THE INVENTION

The invention then, comprises the following, inter alia, separately or in combination:

A solid pharmaceutical composition in dosage form having a matrix-controlled extended two-stage release profile comprising an effective amount of at least one pharmaceutically-active ingredient or principle, wherein the matrix consists essentially of a combination of a water-soluble salt of casein and a water-insoluble salt of casein, the total water-soluble and water-insoluble casein salt content comprising between 5% and 98% of the total weight of the pharmaceutical composition, all salts and cations being pharmacologically acceptable; such a composition wherein the water-soluble and water-insoluble casein salts comprise between 10% and 90% by weight of the pharmaceutical composition, preferably between 30% and 80% by weight; such a composition wherein the pharmaceutical composition comprises between about 5% and 95% of a water-insoluble casein salt based upon the total casein salt content, preferably between about 20% and 70% by weight; such a composition wherein the water-insoluble casein salt is calcium caseinate; such a composition wherein the water-soluble calcium salt is sodium caseinate; such a composition wherein the pharmaceutical composition comprises an enzyme; such a composition wherein the enzyme is pancreatin or pepsin or both, and such a composition wherein the active ingredient is memantine.

Moreover, a process for the preparation of a solid pharmaceutical composition in dosage form having a matrix-controlled two-stage release profile comprising an effective amount of at least one pharmaceutically-active ingredient or principle, wherein the matrix consists essentially of a combination of a water-soluble salt of casein and a water-insoluble salt of casein, comprising the step of compressing, granulating, extruding, pelletizing, or tabletting, in dry or wet manner, of a mixture comprising the at least one active ingredient in admixture with both a water-soluble and a water-insoluble salt of casein or, alternatively, a water-soluble salt of casein and a salt or solution of a polyvalent cation which is adapted to form a water-insoluble salt of casein in situ, the total water-soluble and water-insoluble casein salt content of the admixture in the final composition comprising between 5% and 98% of the total weight of the pharmaceutical composition, all salts and cations being pharmacologically acceptable; such a process wherein the water-soluble and water-insoluble casein salts are included in the mixture to the extent of between 10% and 90% by weight of the pharmaceutical composition, preferably between 30% and 80% by weight; such a process wherein between about 5% and 95% of a water-insoluble casein salt, based upon the total casein salt content, is mixed into the composition, preferably between about 20% and 70% by weight; such a process wherein the water-insoluble casein salt mixed into the composition is calcium caseinate, and such a process wherein the water-soluble casein salt is sodium caseinate; such a process wherein a water-soluble casein salt and a polyvalent cation salt is employed in the process, the percentage of the water-insoluble casein salt content to the final resultant casein salt content being between about 5% and 90%, preferably between 20% and 70%; such a process wherein the cations are calcium ions; such a process wherein the water-soluble casein salt employed is sodium caseinate; such a process wherein an enzyme is also mixed into the pharmaceutical composition; such a process wherein the enzyme is pancreatin or pepsin or both; and such a process wherein the active ingredient mixed into the composition is memantine.

The Present Invention

According to the practice of the present invention, the problem is solved by providing a solid pharmaceutical composition in dosage form containing a pharmaceutically-effective amount of one or more active substances and the usual auxiliary agents and additives, but also a total of between 5 and 98%, preferably 10 to 90%, and especially 30 to 80%—based on the total weight of the composition—of a combination of a water-soluble and a water-insoluble salt of casein. A pharmaceutical formulation of this type can then be treated in the usual way to provide a variety of solid dosage forms having a two-phase matrix-controlled extended release profile. This includes the employment of procedures known in the pharmaceutical industry, such as compressing, granulating, extruding, pelletizing, and tabletting in dry or wet manner. It is of course also possible to combine a variety of procedures to provide the desired product formulation in any one of various forms such as tablets, dragees, pellets, granules, and the like. The amount of active substance present can be varied widely depending on the indication to be treated and the type of dosage form desired, for example, from 0.01 to 90%, based on the total weight of the pharmaceutical composition.

Quite unpredictably, it has been found that the pharmacokinetic properties of the solid dosage forms according to the present invention are not affected by the manufacturing method employed or the variations arising in practice, e.g., the compression forces utilized.

The casein employed can be a commercially available product, and the molecular weight and water content thereof may vary considerably, for example between MW 18000 and MW 30000 Daltons—depending upon the origin thereof, without detracting from its operativeness according to the present invention. Casein is of course a substance approved for use under food legislation throughout the civilized world.

A casein salt of a monovalent cation, such as lithium, potassium, ammonium, and preferably sodium, is used as the water-soluble casein salt.

The water-insoluble caseinate is a salt of casein with a bi- or polyvalent cation, both referred to herein as a polyvalent cation. These include, e.g., calcium, magnesium, zinc, manganese, aluminum, iron, or mixtures thereof. Particularly preferred is calcium. The water-insoluble caseinate can be used as such.

In addition, it is possible to include in the composition, containing a soluble casein salt, a physiologically-compatible polyvalent cation, in the form of a salt thereof which is soluble in water or gastric fluid, optionally in solution in water, in amounts such that a part of the soluble caseinate is converted to an insoluble caseinate, thereby transforming a part of the soluble casein salt to an insoluble casein salt in situ, as by gastric fluid upon ingestion. A part or all of the insoluble salt may be provided in this manner. Preferred cations are the chloride, gluconate, carbonate, lactate, and saccharate cations and, in particular, calcium chloride, calcium gluconate, calcium hydrogen phosphate, calcium lactate, calcium D-saccharate, calcium levulinate, and their hydrates, or mixtures thereof, are preferred salts for providing the aqueous polyvalent, including bivalent, cation, which may be used as such or, if desired, be solvated by simple dissolution of the salt, e.g., in water, and optionally used in a normal granulation procedure.

The weight/weight ratio of soluble to insoluble caseinate is between 5 and 95%, preferably between 5 and 90%, and more preferably between 20 and 70%, based on the total caseinate content of the composition. Most preferred is a weight/weight ratio of between 30 and 60%. The amounts of the aforementioned ionic compounds and their solutions required for the production of the desired amount and ratio of insoluble caseinate in situ are dependent on the type of cation, its counter-ion, and the molecular weight of the casein employed, as will be readily understood by and as can be readily determined by one skilled in the art since it involves only basic chemistry.

According to the invention, quite unpredictably and advantageously, a controlled bi-phase matrix-controlled extended release of active pharmaceutical ingredient is thus achieved with the specified combination of matrix-forming substances alone and without the necessity of any embedded or surrounding external protein.

Common auxiliary agents and additives or excipients which may be employed to complete the pharmaceutical composition used as matrix are components well known in the pharmaceutical industry. These include, for example, tabletting aids, such as highly disperse silicic acid, magnesium stearate, microcrystalline cellulose, lactose, talc, colorants such as iron oxides or quinoline yellow, pigments such as titanium dioxide and calcium carbonate, glycerylmonostearate, glyceryl behenate, sodium stearylfumarate, stearic acid, cetyl palmitate, long-chain partial glycerides, cellulose powder, mannitol, calcium phosphate, silicon dioxide, colloidal silicon dioxide, silicon dioxide hydrate, and polyethylene glycol, preferably of a molecular weight 1,500 to 6,000 Dalton, and the like.

Active ingredients or mixtures thereof, which can be used to provide an effective amount of the active pharmaceutical principle or ingredient in the compositions of the invention, encompass innumerable pharmaceutically-active compounds which are suitable for extremely varied fields of end-use application. They include tranquillizers such as chlorpromazine and benzodiazepines such as diazepam; muscle relaxants such as mephenesin; antihypertensive agents such as $\alpha$-methyldopa; centrally-acting analgetics such as morphine; peripherally-acting analgetics such as paracetamol; non-steroidal antiphlogistics such as ibuprofen; local anesthetics such as benzocaine; spasmolytics such as papaverine; prostaglandins such as PEG2, antibiotics such as penicillin and tetracycline; agents influencing the demential syndrome such as memantine; anti-Parkinsonism therapeutic agents such as amantadine, L-dopa, selegiline, bromocriptine, and metixene; antimalarials such as chloroquine; corticosteroids such as dexamethasone; androgens such as methyltestosterone; estrogens such as ethinylestradiol; gestagens such as levonorgestrel; sympathometics such as adrenalin; substances having cardiovascular effect such as nitroglycerin; diuretics such as hydrochlorothiazide; anthelmintics such as praziquantel: $\beta$-blockers such as timolol; H2-blockers such as cimetidine: vitamins such as ascorbic acid, and the like. Effective amounts of such pharmaceutically-active principles or ingredients are well known in the art.

Most preferred is memantine.

The readily-produced formulations according to the invention, upon ingestion, advantageously result in a controlled two-phase release of the active ingredient, with an amount of active substance adapted to the therapeutic goal being released and available in the first phase, i.e., in the stomach, as well as in the second phase, i.e., in the intestines where, after a slight delay, a renewed liberation of active ingredient is effected, the remainder of the active ingredient being released over a predetermined time period, thereby attaining an effective adaptation to the total active substance availability requirements, with the partial release in each stage resulting in corresponding desirable plasma levels. Local excess concentrations of active substance are thus avoided.

This two-phase pharmaceutically-active ingredient, e.g., drug or vitamin, liberation profile is substantially independent of the enzymes contained in the physiological environment of the stomach and intestines, as shown in the following examples, a result which hitherto has not been realizable by conventional dosage formulations.

However, if a change in the release rate is required in one or the other of the two liberation phases which might be necessary or desirable in view of the type of active substance employed, the physiology of the patient, or the degree of seriousness of the ailment treated, enzymes such as pepsin and/or pancreatin can of course be included in the formulation in suitable amounts, as well as numerous other enzymes or polymer-enzyme products such as neutral, acid, or alkaline protease, or any of the foregoing enzymes insolubilized by attachment to an ethylenemaleic acid or anhydride (EMA) polymer (as in U.S. Pat. No. 3,751,561). This does not change the two-phase profile. It is only the rate of liberation within the phases which can thus be slightly varied.

The mechanism of the extended two-stage release can be explained as follows:

The use of a water-insoluble caseinate, e.g., calcium caseinate, results in the formation of a matrix tablet. The drug is released independently of the pH of the dissolution medium in a diffusion-controlled manner. In other words, due to the presence of the insoluble caseinate, there is an extended release in both stages, the extent of retardation being dependent on the amount of insoluble caseinate in the formulation, as shown in Study 5 and corresponding FIG. 5.

In alkaline medium, the insoluble caseinate gradually becomes degraded, equivalent to an attenuation of the matrix-effect. Subsequently, the retardation is diminished and the drug release rate increases, which can be seen in the second stage, although also in this second stage drug release is extended.

BRIEF DESCRIPTION OF THE DRAWINGS

Reference is now made to the accompanying drawings, for a better understanding of the present invention, wherein.

SPECIFIC DESCRIPTION OF THE INVENTION

The invention will now be described in greater detail with references to the following Examples, which are not to be construed as limiting.

I. Production of the Drug Formulation

Example 1

| Active Substances and Additives | Percent by Weight |
|---|---|
| memantine HCl | 20.0 |
| sodium caseinate | 46.8 |
| calcium caseinate | 31.2 |
| Aerosil 200 TM (finely-divided SiO$_2$) | 1.0 |
| magnesium stearate | 1.0 |

All components with the exception of magnesium stearate are homogeneously distributed in a suitable mixer such as a Diosna TM mixer; subsequently magnesium stearate is added and the mixture passed through a screen of an average (U.S. Standard Sieve Series) mesh size of 300 µm. After a further mixing of the material to be compressed, tablets having a mass of 100 mg and a diameter of 6 mm are produced on a suitable tabletting machine, using a force of compression of 8 kN.

Example 2

| Active Substances and Additives | Percent by Weight |
|---|---|
| caffeine | 20.0 |
| sodium caseinate | 75.0 |
| calcium chloride × 2H$_2$O | 3.0 |
| Aerosil 200 TM | 1.0 |
| magnesium stearate | 1.0 |

The caffeine and sodium caseinate components are mixed in a suitable fluidized bed granulation machine, such as the Aeromatic STREA 1 TM. The granulation of a 500 g batch is effected with 400 ml of an aqueous fluid containing 3 g calcium chloride dihydrate in dissolved form at a pump rate of 10 ml/min, an inlet temperature of 60° C., an outlet temperature of 32° C., and at an atomizing pressure on the binary nozzle of about 2 bar. After a redrying of 10 min at 60° C. and a weak supply of fresh air, the granulate is separated from the coarse portion (>1.0 mm) and from the fine portion (<0.15 mm) and, after admixing with Aerosil and magnesium stearate, is compressed using a force of compression of 8 kN into tablets having a weight of 100 mg and a diameter of 6 mm.

Example 3

| Active Substances and Additives | Percent by Weight |
|---|---|
| piroxicam | 20.0 |
| sodium caseinate | 65.0 |
| calcium hydrogen phosphate + 2H$_2$O | 3.8 |
| Avicel PH 102 TM - microcrystalline cellulose | 9.2 |

-continued

| Active Substances and Additives | Percent by Weight |
|---|---|
| Aerosil 200 | 1.0 |
| magnesium stearate | 1.0 |

All components except for magnesium stearate are homogeneously distributed in a suitable mixer, e.g., a Diosna TM mixer, magnesium stearate then added, and the mixture passed through a screen of an average (U.S. Standard Sieve Series) mesh size of 300 µm. After a further mixing of the compressed mass, tablets are produced on a suitable pelleting machine, having a mass of 100 mg and a diameter of 6 mm, with a compression force of 8 kN being applied.

Example 4

| Active Substances and Additives | Percent by Weight |
|---|---|
| ibuprofen | 77.0 |
| sodium caseinate | 20.0 |
| calcium chloride + 2H$_2$O | 1.0 |
| Aerosil 200 TM | 1.0 |
| magnesium stearate | 1.0 |

By spraying a suitable granulating liquid such as an ethanol/water mixture (v/v 3/2) or a colloid-containing granulating liquid such as gelatine/water (1/30), a crust granulate or an adhesive granulate is first produced from the ibuprofen.

The granulate is mixed with the remaining components in a suitable mixer and is compressed, using a compression force of 15 kN, into tablets having a mass of 520 mg and a diameter of 12 mm.

Example 5

| Active Substances and Additives | Percent by Weight |
|---|---|
| memantine-HCl | 20.0 |
| sodium caseinate | 48.0 |
| calcium caseinate | 32.0 |

All components are homogeneously distributed using a suitable mixer and, in a mixing kneader, are then intimately wetted with a suitable plasticizing liquid, such as purified water or an ethanol/water mixture (v/v 3/2) to an extent of about 60% v/v based on the solid portion. The resultant mass is lyo-extruded either on a screw extruder or on a distributing roll-type extruder with an apertured disk-diameter of 1.5 mm. The thus-obtained strands are divided and filleted on a spheronizer to form pellets of a diameter of 1.8 mm. Subsequently, the pellets are either loaded into capsules or are compressed into tablets after admixing with 1% Aerosil and 1% magnesium stearate.

II. Liberation or Release Tests

The media used in all dissolution tests is either simulated gastric fluid (pH 1.2) or simulated intestinal fluid (pH 7.5). To more closely approach in vivo conditions, pepsin (gastric fluid) and pancreatin (intestinal fluid) are added. In the chapter "Test Solutions" of the U.S. Pharmacopoea XXII, the compositions of the two media are exactly described as follows:

"Gastric Fluid, Simulated, TS—Dissolve 2.0 g of sodium chloride and 3.2 g of pepsin in 7.0 mL of hydrochloric acid and sufficient water to make 1000 mL. This test solution has a pH of about 1.2."

"Intestinal fluid, Simulated, TS—Dissolve 6.8 g of monobasic potassium phosphate in 250 mL of water, mix, and add 190 mL of 0.2N sodium hydroxide and 400 mL of water. Add 10.0 g of pancreatin, mix, and adjust the resulting solution with 0.2N sodiumhydroxide to a pH of 7.5±0.1. Dilute with water to 1000 mL."

1. Retarded Release of an Active Substance in Response to the Insoluble Caseinate Content The following basic formula is compressed:

| | |
|---|---|
| caffeine | 20.0 |
| Ca-caseinate | 0–78.0% (based on the total casein content) |
| Aerosil 200 | 1.0 |
| magnesium stearate | 1.0 |
| NaCaseinate | ad 100% |

Eight different compressive masses of varying Na-caseinate and Ca-caseinate proportions (added as such) are formulated by using the tabletting auxiliaries Aerosil and magnesium stearate. As no other auxiliaries are added, a true picture of the release properties is obtained.

The total caseinate portion amounts to 78%. The pulverulent mixtures are compressed on an instrumentized Exacta 1 ™ at an adjusted speed of 30 strokes/min, using compressing tools of 6 mm, flat without facette, at a constant force of compression of 8 kN to form tablets having an individual weight of 100 mg.

Dosage form products are obtained having a Ca caseinate content of 0, 10, 20, 30, 40, 50, 70 and 100%, the liberation profile of which is determined at pH 1.2 (simulation of gastric environment).

Figure 5:
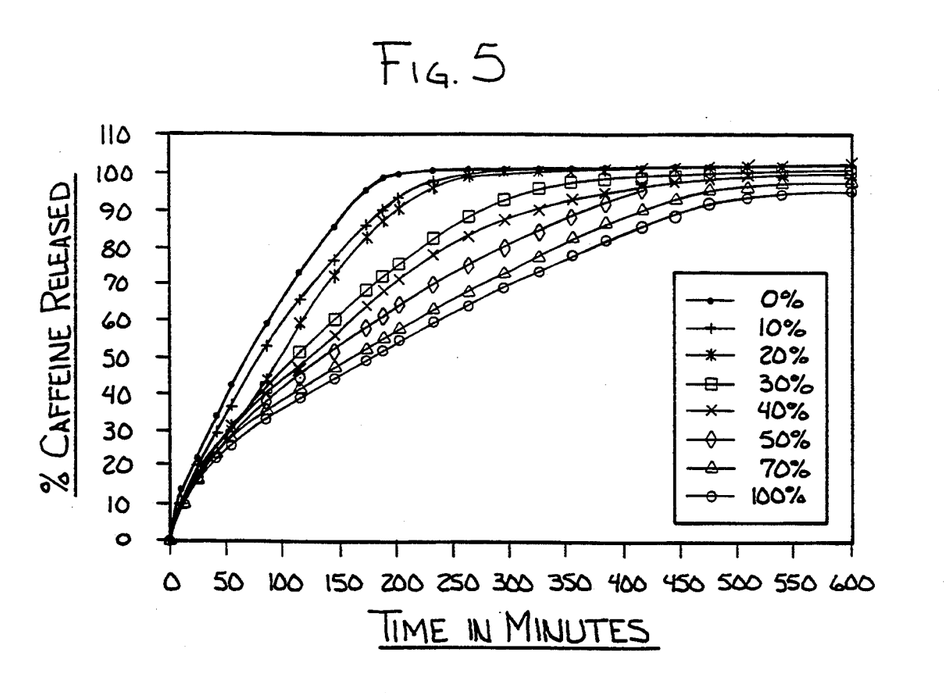
FIG. 5 is a graph illustrating the dependence of drug release on the insoluble caseinate content of a dosage form according to the invention, showing the percent caffeine released over a period of time with calcium caseinate content of the formulation varying from 0 to 100%, this liberation profile being determined in a simulated gastric environment at a pH of 1.2 without added enzyme.

FIG. 5 shows the dependence of drug release on the insoluble caseinate, i.e., calcium caseinate, content of the dosage form, and thus the extent of retardation. The tablet formulations employed in this study correspond to the basic formula of II. 1 just hereinabove provided.

The dissolution of 80% of total caffeine content occurs in the case of 20% Ca-caseinate (percentage related to total caseinate) at 160 min (vs. 127 min without Ca-caseinate—F=1.25), at 285 min with 50% Ca-caseinate (F=2.2), and at 350 min with a Ca-caseinate content of 100% (F=2.75). These data are the results of dissolution tests in gastric fluid (pH 1.2) without added enzyme.

It has thus been established that the release in this gastric environment can be inhibited by the combination of insoluble caseinate with soluble caseinate; depending on the relative proportions thereof, a varying retardation is obviously achieved. This permits the selection of a highly-desirable individual release profile, depending on the active substance and the type of indication to be treated.

2. Liberation or Release Profile of Caseinate Tablets Compressed at a Varying Force of Compression The following formulation with a Ca-caseinate proportion of the total caseinate content of 40% is compressed in accordance with the aforementioned conditions at forces of compression of between 4 and 12 kN into tablets having an individual weight of 100 mg:

| | |
|---|---|
| caffeine | 20.0 |
| Na-caseinate | 46.8 |
| Ca-caseinate | 31.2 |
| Aerosil 200 | 1.0 |
| magnesium stearate | 1.0 |

It has been found that varying forces of compression within these ranges have no bearing or effect on the release profile.

3. Addition of Polyvalent Salt to the Soluble Caseinate to Produce the Insoluble Caseinate In Situ The following basic matrix formulation is produced in the foregoing manner with admixture and/or granulation and in accord with the foregoing conditions (see Examples 1–5):

| | |
|---|---|
| caffeine | 20.0 |
| NaCaseinate | 65.0 |
| Ca-salt, optionally in aqueous solution | X |
| Aerosil | 1.0 |
| magnesium stearate | 1.0 |
| Avicel PH 102 | ad 100% |

When completely converting a soluble caseinate, for example the NaCaseinate, to an insoluble, e.g., calcium, salt, the insoluble cation content can be readily determined, e.g., the calcium content is normally 1.5% to 1.7% by weight, but can optionally be made even higher, so that an amount as suggested below according to the present invention can be readily determined and the desired amount of insoluble casein salt thereby calculated and thus-provided.

The following pharmaceutically-suitable calcium salts can, for example, be used in the foregoing formulation to provide an insoluble casein salt in situ in a formulation of the invention:

| Amount X employed in the Formula: | |
|---|---|
| calcium chloride $\times$ 2H$_2$O | 3.6 |
| calcium gluconate $\times$ H$_2$O | 10.9 |
| calcium carbonate | 2.4 |
| calcium hydrogen phosphate $\times$ 2H$_2$O | 4.2 |
| calcium lactate $\times$ 5H$_2$O | 7.5 |
| calcium nitrate $\times$ 4H$_2$O | 5.8 |
| calcium-D-saccharate | 6.1 |
| calcium levulinate | 7.5 |

The compositions of the foregoing formulae are compressed under the aforementioned conditions at a constant force of compression of 8 kN into tablets having an individual weight of 100 mg and are found to have the same two-phase extended release profile as a unit dosage matrix containing the same proportions of soluble and insoluble casein salts in solid form but present as such in the beginning admixture.

It has been found that all calcium salts used in this manner produce insoluble casein salt-containing matrices having almost identical liberation profiles. The $t_{50}$-values vary within a narrow range of between 100 and 113 min, while the $t_{90}$-values vary between 262 and 295 min.

Identical results are also obtained with solutions of other polyvalent ions besides calcium, for example, magnesium, zinc, and aluminum salts.

4. Influence of the Incubation Medium

A variety of compressed dosage form products produced according to II.1 with varying proportions of insoluble caseinate, preferably calcium caseinate, are now examined as to their drug-liberation profile with changing media both with and without enzymes.

Figure 1:
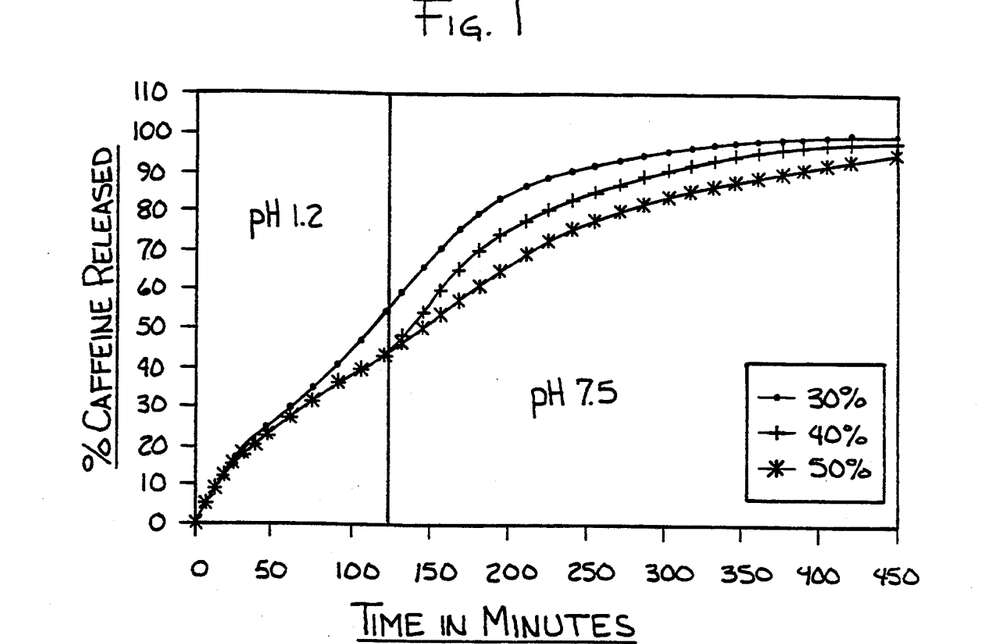
FIG. 1 is a graph of a biphasic drug liberation profile showing release of caffeine over a period of time in accord with Study 1 of this application without enzyme and with medium change after two hours.
Figure 2:
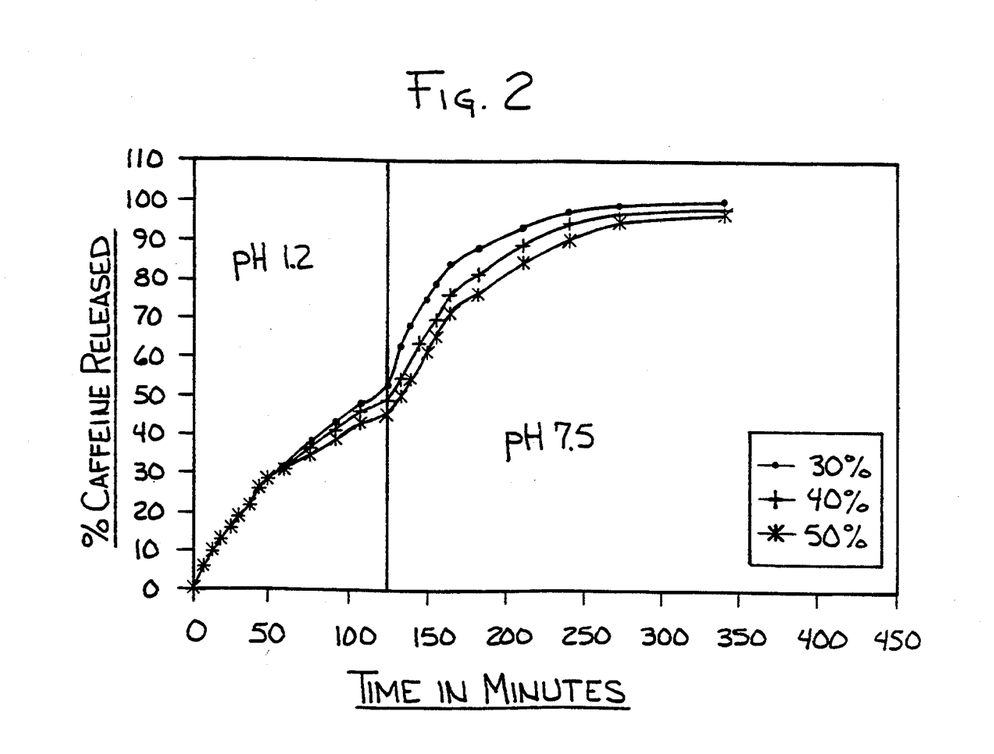
FIG. 2 is the same according to Study 2 of this application with enzyme and with medium change after two hours.

The results are shown in Studies 1 and 2 and their corresponding figures FIG. 1 and FIG. 2. The figures (FIGS. 1 and 2) resulting from these studies show the biphase profiles of the compositions produced according to the invention with a Ca-caseinate portion of 30, 40 and 50% by weight, the results being shown in the following TABLE 1 (medium change after 2 hours):

TABLE 1

| pH Ca-caseinate (%) | $t_{50}$ (min) | | | $t_{90}$ (min) | | |
|---|---|---|---|---|---|---|
| | 30 | 40 | 50 | 30 | 40 | 50 |
| 1.2/7.5 without enzyme (Study 1) (FIG. 1). | 111 | 138 | 143 | 232 | 300 | 376 |
| 1.2/7.5 with enzyme (Study 2) (FIG. 2). | 112 | 123 | 132 | 195 | 220 | 239 |

Thus, FIG. 1 shows the dissolution curves of three tablet formulations (produced according to II.1) with varying Ca-caseinate contents: 30, 40 and 50%.

Dissolution media used are simulated gastric (phase 1) and intestinal (phase 2) fluids without enzymes.

In FIG. 2 the dissolution behavior of the abovementioned tablet formulations are graphically shown again, but in this case the dissolution media respectively contained pepsin (phase 1) and pancreatin (phase 2).

It can be clearly derived from FIGS. 1 and 2 that mainly in alkaline (intestinal) medium the rate of drug release can be controlled by the content of water-insoluble Ca-caseinate. The higher the Ca-caseinate concentration in the tablet formulation, the slower the drug release. In other words: Ca-caseinate is exhibiting a retarding effect.

A comparison between FIGS. 1 and 2 shows that control of drug release-rate by varying the Ca-caseinate content is not influenced by the presence of enzymes in the dissolution media, thus mimicking in vivo conditions. Only the time to attain complete drug release is reduced by a factor F=1.3.

Thus, surprisingly enough, it has been found that the desired liberation profile is relatively independent of the enzyme present. The low enzyme-induced acceleration virtually ensures a 100% release in the second phase after about five (5) hours.

5. Release of Memantine from Tablets According to the Invention (Study 3)

A formulation produced according to Example I.1. is tested, as above, at pH 1.2/pH 7.5 (without enzyme, medium change after 2 hours). The two-phase liberation profile is shown in FIG. 3.

6. Release of Caffeine from a Formulation According to the Invention (Study 4)

A formulation produced according to Example I.2 is tested, as above, at pH 1.2/pH 7.4 (without enzyme, medium change after 2 hours). Here, too, a two-phase liberation profile arises as shown in FIG. 4.

Figure 3:
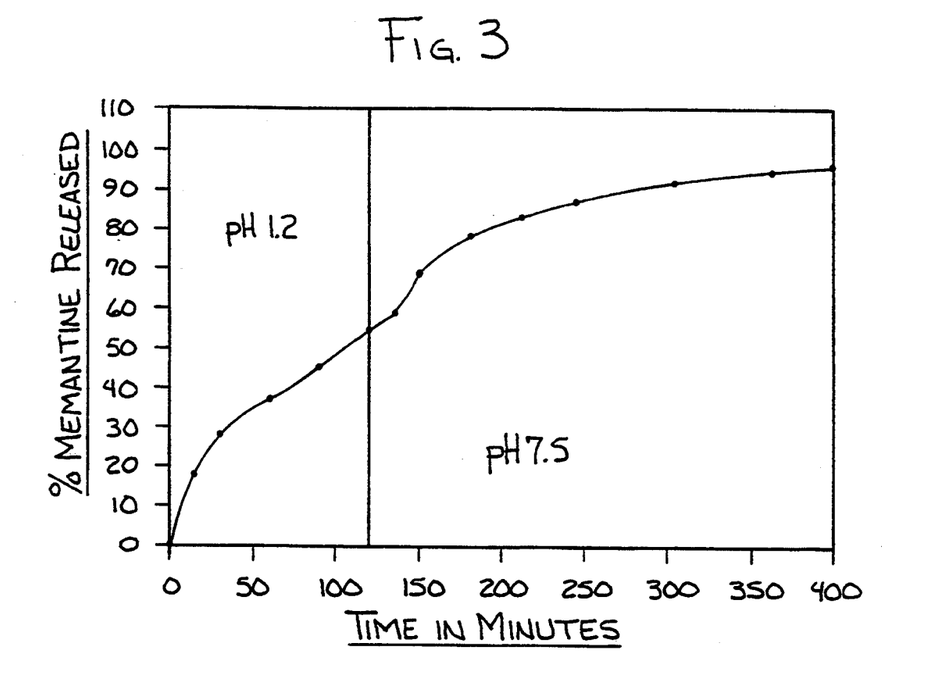
FIG. 3 is a graph showing the biphasic release of Memantine over a period of time in accord with Study 3 of this application without enzyme and with medium change after two hours.
Figure 4:
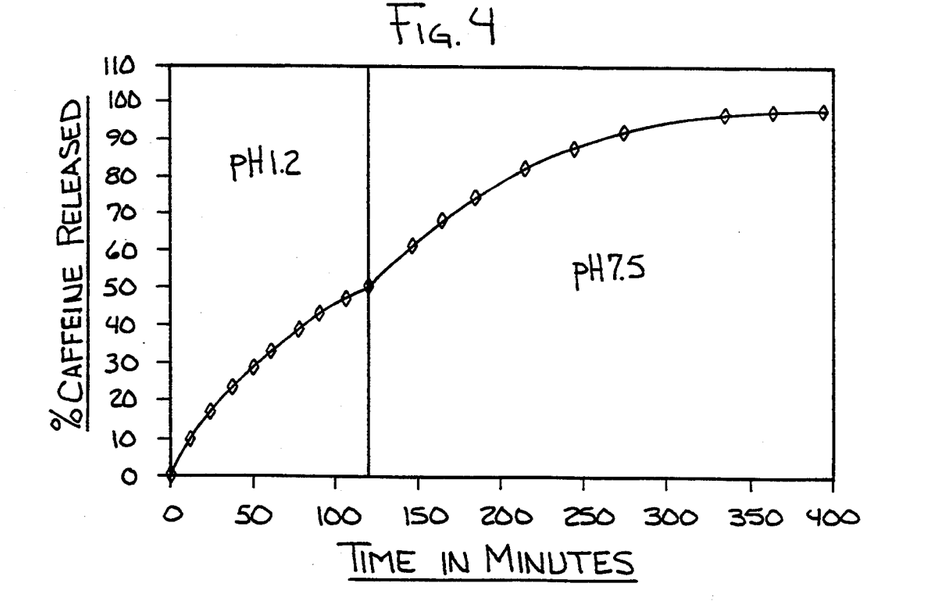
FIG. 4 is the same as FIGS. 1 and 2, but in accord with Study 4 of this application without enzyme and with medium change after two hours.

FIG. 3 graphically shows the release profile of a memantine formulation produced according to I.1, and FIG. 4 the dissolution curve of a caffeine formulation prepared according to I.2. In both cases, the dissolution media contained no enzymes.

Within the scope of simulated in vivo conditions, the change of dissolution media in each study represents the passage of a solid dosage form from the stomach into the intestine.

Especially the graphs of FIGS. 2 and 4, but also the plots of the other FIGS., clearly demonstrate that a change of pH results in a steeper slope of the dissolution curve, which means an accelerated drug release. Translating this into human use, the value of the extended-two-stage release is seen as a slower increase of drug concentration into the blood, thus reducing undesirable side effects. This is particularly true for gastric side effects because, according to FIGS. 1–4, only about 40–50% of the drug content is released in the stomach.

Beyond this, a reliable slow release, generally prolongs intervals between application or dosing and thus improves patient compliance considerably.

7. Study 5, which was productive of FIG. 5, showing the Direct Influence of Insoluble Casein on the Drug Release Profile, has already been fully discussed hereinbefore under the heading of II 1.

Accordingly, it is clear that formulations having an optimally-adapted release profile can be produced in simple manner by incorporation of physiologically-compatible components into two-phase extended-release compositions and dosage forms according to the present invention.

It is seen from the foregoing that the objects of the present invention have been accomplished and that novel, efficient, and economic solid pharmaceutical compositions in dosage form, which exhibit an extended matrix-controlled two-phase release profile and which are characterized by the presence in the matrix of both a water-soluble and a water-insoluble salt of casein, which water-insoluble salt of casein may be provided in situ therein, and a process for the production thereof have been thereby provided, whereby all of the previously-mentioned advantages have been attained and the shortcomings of the prior art have been obviated.

Although the preferred embodiments of the invention have been illustrated in the accompanying drawings and described in the foregoing Specification, it is to be understood that the invention is not limited to the embodiments disclosed or to the exact details of operation or exact compounds, compositions, methods, or procedures shown and described, inasmuch as the invention is capable of numerous modifications and substitutions of equivalents without departing from the spirit or scope thereof, as will readily be apparent to one skilled in the art, wherefore the present invention is to be understood as limited only by the full scope which can be legally accorded the appended claims.

We claim:

1. A solid pharmaceutical composition in a dosage form selected from a compressed tablet formed from (a) granules, (b) pellets, or (c) spheronized extruded strands, or in the form of small (a) through (c) themselves, optionally in a capsule filled therewith, having a matrix-controlled extended two-stage release profile having a matrix comprising an effective amount between 0.01 and 90% of the total weight of the pharmaceutical composition of (C) at least one pharmaceutically-active ingredient, wherein the matrix consists essentially of a combination of a water-soluble salt of casein (A) and a water-insoluble salt of casein (B), the total water-soluble casein salt (A) and water-insoluble casein salt (B) content comprising between 5% and 98% of the total weight of the pharmaceutical composition, the water-insoluble casein salt comprising between about 5% and 95% based upon the total casein salt content, all salts and cations being pharmacologically acceptable.

2. A pharmaceutical composition of claim 1, wherein the water-soluble and water-insoluble casein salts comprise between 10% and 90% by weight of the pharmaceutical composition.

3. A pharmaceutical composition of claim 2, wherein water-soluble and water-insoluble casein salts comprise between 30% and 80% by weight of the pharmaceutical composition.

4. A pharmaceutical composition of claim 1, wherein the percentage of water-insoluble casein salt to total casein salt content is between about 20% and 70% by weight.

5. A pharmaceutical composition of claim 1, wherein the water-insoluble casein salt is calcium caseinate.

6. A pharmaceutical composition of claim 1, wherein the water-soluble calcium salt is sodium caseinate.

7. A pharmaceutical composition of claim 1, wherein the pharmaceutical composition comprises an enzyme.

8. A pharmaceutical composition of claim 7, wherein the enzyme is pancreatin or pepsin or both.

9. A pharmaceutical composition of any of claims 1 through 3 and 4 through 8, wherein (A) is sodium caseinate and (B) is calcium caseinate and the active ingredient (C) is memantine.

10. A process for the preparation of a solid pharmaceutical composition in a dosage form selected from a compressed tablet formed from (a) granules, (b) pellets, or (c) spheronized extruded strands, or in the form of small (a) through (c) themselves, optionally in a capsule filled therewith, having a matrix-controlled two-stage release profile having a matrix comprising an effective amount between 0.01 and 90% of the total weight of the pharmaceutical composition of at least one pharmaceutically-active ingredient (C), wherein the matrix consists essentially of a combination of a water-soluble salt of casein (A) and a water-insoluble salt of casein (B), comprising the step of compressing, granulating, extruding, pelletizing, or tabletting, in dry or wet manner, of a mixture comprising the at least one pharmaceutically-active ingredient (C) in admixture with both a water-soluble salt of casein (A) and a water-insoluble salt of casein (B) or, alternatively, a water-soluble salt of casein (A) and a salt or solution of a polyvalent cation which is adapted to form a water-insoluble salt of casein (B) in situ, the total water-soluble and water-insoluble casein salt content of the admixture in the final composition comprising between 5% and 98% of the total weight of the pharmaceutical composition, the percentage of water-insoluble casein salt (B) to total casein salt content included in the mixture being between about 5% and 95% based upon the total casein salt content, all salts and cations being pharmacologically acceptable.

11. A process of claim 10, wherein the water-soluble and water-insoluble casein salts are included in the mixture to the extent of between 10% and 90% by weight of the pharmaceutical composition.

12. A process of claim 11, wherein the water-soluble and water-insoluble casein salts are included in the mixture to the extent of between 30% and 80% by weight of the pharmaceutical composition.

13. A process of claim 10, wherein the percentage of water-insoluble casein salt to total casein salt content included in the mixture is between about 20% and 70% by weight.

14. A process of claim 10, wherein the water-insoluble casein salt mixed into the composition is calcium caseinate and wherein the water-soluble casein salt is sodium caseinate.

15. A process of claim 10, wherein a water-soluble casein salt and a polyvalent cation salt is employed in the process, the percentage of the water-insoluble casein salt content to the final resultant casein salt content being between about 5% and 90%.

16. A process of claim 15, wherein the percentage is between 20% and 70%.

17. A process of claim 15, wherein the cation is the calcium ion.

18. A process of claim 15, wherein the water-soluble casein salt employed is sodium caseinate.

19. A process of claim 10, wherein an enzyme is also mixed into the pharmaceutical composition.

20. A process of claim 19, wherein the enzyme is pancreatin or pepsin or both.

21. A process according to any of claims 10 through 12 and 13 through 20, wherein (A) is sodium caseinate and (B) is calcium caseinate and the active ingredient (C) mixed into the composition is memantine.

22. A method of administering a pharmaceutically-active ingredient (C) consisting essentially of the step of administering the pharmaceutically-active ingredient (C) in the form of a two-phase extended-release pharmaceutically-effective solid dosage form of claim 1, or claim 5, or claim 6.

* * * * *